United States Patent
Min et al.

(10) Patent No.: US 6,689,427 B2
(45) Date of Patent: Feb. 10, 2004

(54) GROUP IV METAL PRECURSORS AND A METHOD OF CHEMICAL VAPOR DEPOSITION USING THE SAME

(75) Inventors: Yo Sep Min, Seoul (KR); Young Jin Cho, Incheon-Shi (KR); Dae Sig Kim, Kyungki-Do (KR); Ik Mo Lee, Incheon-Shi (KR); Sun Kwon Lim, Incheon-Shi (KR); Wan In Lee, Seoul (KR); Bo Hyun Choi, Gyeongsangnam-Do (KR)

(73) Assignee: Samsung Electronics Co., Ltd., Kyungki-Do (KR)

( * ) Notice: Subject to any disclaimer, the term of this patent is extended or adjusted under 35 U.S.C. 154(b) by 0 days.

(21) Appl. No.: 09/933,736

(22) Filed: Aug. 22, 2001

(65) Prior Publication Data

US 2002/0058843 A1 May 16, 2002

(30) Foreign Application Priority Data

Aug. 26, 2000 (KR) ........................................ 2000-49832
Jan. 17, 2001 (KR) ........................................ 2001-2574

(51) Int. Cl.[7] ........................ C23C 16/00; H01L 21/44; C07F 7/00
(52) U.S. Cl. ........................ 427/592; 427/587; 438/681; 438/685; 556/56; 564/278
(58) Field of Search ........................ 556/56; 564/278; 427/587, 592; 438/681, 685

(56) References Cited

U.S. PATENT DOCUMENTS 4,950,790 A   8/1990   Norman ...................... 564/278

OTHER PUBLICATIONS

Doherty et al., Organometallics, vol. 18, No. 6, pp. 1018–1029 (1999).*

* cited by examiner

Primary Examiner—Porfirio Nazario-Gonzalez
(74) Attorney, Agent, or Firm—Birch, Stewart, Kolasch & Birch, LLP

(57) ABSTRACT

An organometallic precursor of a formula $M(L)_2$ for use in formation of metal oxide thin films, in which M is a group IV metal ion having a charge of +4 and L is a tridentate ligand having a charge of –2, the ligand being represented by the following formula (I):

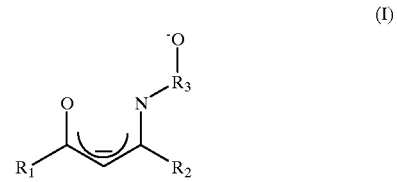

wherein each of $R_1$ and $R_2$, independently, is a linear or branched $C_{1-8}$ alkyl group; and $R_3$ is a linear or branched $C_{1-8}$ alkylene group. Also disclosed is a chemical vapor deposition method wherein a metal oxide thin film is formed on a substrate using the organometallic precursor. The precursor exhibits excellent volatility, thermal property and hydrolytic stability and is particularly suitable for the deposition of a multi-component metal oxide thin film containing a group IV metal such as titanium.

7 Claims, 8 Drawing Sheets

GROUP IV METAL PRECURSORS AND A METHOD OF CHEMICAL VAPOR DEPOSITION USING THE SAME

BACKGROUND OF THE INVENTION

Priority Korean Patent Application Nos. 2000-49832 filed Aug. 26, 2000 and 2001-2574 filed Jan. 17, 2001, are incorporated herein in their entirety by reference.

FIELD OF THE INVENTION

The present invention relates to a novel group IV metal precursor and to a chemical vapor deposition method using the precursor. More particularly, the present invention relates to a chemical vapor deposition method which comprises forming a metal oxide thin film on a substrate using a group IV metal precursor which contains a tridentate N-alkoxy-β-ketoiminate ligand having a charge of −2.

Description of the Prior Art

With development in the telecommunication industry, there is an increased need for the development of new electronic materials. Also, as electronic devices are continuously reduced in both size and thickness, it has become important to advance metal oxide processing technologies and, in particular, thin film formation technologies.

A Metal-Organic Chemical Vapor Deposition (MOCVD) method using volatile organometallic compounds as precursors is widely used in the deposition of metal oxide thin films, which are applied as high dielectric thin films, superconductive thin films, electrodes, and the like. Depending on the vaporization of precursor materials, the MOCVD method is generally classified into a bubbler method and a vaporizer method. In the bubbler method, solid or liquid precursor materials are bubbled with a delivery gas to be sublimed. In the vaporizer method, precursor materials dissolved in suitable solvents are dropped onto a hot plate heated to a high temperature, so that the precursors are vaporized together with the solvents, thereby inducing efficient vaporization of the precursors. Since the vaporizer method adopts the delivery of the precursors in liquid phase, it is also known as the liquid delivery method.

In order to form thin films on substrates by chemical vapor deposition, it is first necessary to provide precursors having excellent properties. Also, good surface morphology, metal content and step coverage of the thin films formed using the precursors are necessary for their potential application as devices.

Properties of the precursors necessary for use in chemical vapor deposition include high volatility, distinct difference between vaporization temperature and decomposition temperature, low toxicity, chemical stability, thermal stability, easiness of synthesis and thermal decomposition. In addition, during the vaporization or delivery of the precursors, they must not be spontaneously decomposed or subjected to a side reaction with other precursors.

Particularly, for the formation of multi-component thin films having a high quality, metal components deposited from metal precursors on a substrate must be easily controlled in their composition, and also the metal precursors must show similar behaviors in their decomposition at the deposition temperature.

Up to now, a variety of organometallic compounds, such as metal alkyls, metal alkoxides, metal carboxylates, and metal beta-diketonates have been reported as precursors. However, these compounds did not sufficiently meet the property requirements, such as volatility, chemical and thermal stabilities, and toxicity, etc.

There were recently reported precursors of the formula $M(OR)_n$ and precursors of the formula $M(OR)_x(\beta\text{-diketonate})_y$ in which the metal alkoxide is partially substituted with a bidentate ligand, such as β-diketonate. However, such precursors still have problems in that they are susceptible to moisture due to the alkoxide ligand present in the metal complex.

When intermolecular repulsive force of precursors is increased with fluorinated alkyls substituted with fluorine atoms of high electronegativity for hydrogen atoms, volatility of the precursors is generally increased. To improve volatility of metal ions having a small charge-to-radius ratio, such as barium, strontium and the like, there are commonly used methods that introduce a bulky alkyl group-containing ligand or a polydentate Lewis base to saturate unsaturated coordination sites of the metal ions. This saturation inhibits the oligomerization and hydration of the complexes, and reduces the intermolecular interaction. However, such methods result in new problems in that grown thin films may contain fluorine, and that the Lewis base is dissociated during vaporization or delivery of the precursors.

U.S. Pat. No. 4,950,790 assigned to Air Products and Chemicals, Inc. discloses metal β-ketoiminate compounds of the formula $M^{n+}$ (β-ketoiminate)$_n$ which have been improved in thermal and chemical stabilities by filling vacant coordination sites of the metal with β-ketoiminate as a bidentate ligand as a result of the chelate effect thereof. However, such compounds are problematic in that they are low in hydrolytic stability.

There were also reported precursors with a tridentate N-alkoxy-β-ketoiminate ligand having a charge of −2, such as Ta(N-alkoxy-β-ketoiminate)(OEt$_3$) and Nb(N-alkoxy-β-ketoiminate) (OEt$_3$). However, since these precursors contain a highly reactive alkoxide group in addition to the N-alkoxy-β-ketoiminate group as a ligand, they do not contain advantages over the case where only N-alkoxy-β-ketoiminate is used as a ligand.

Furthermore, in depositing a multi-component metal oxide thin film such as barium strontium titanate (BST) thin film by the MOCVD method, there have been used titanium precursors in an excess amount over barium and strontium ones due to the large difference in volatility between the metal precursors, thereby controlling the metal composition of the thin film. However, titanium used in an excess amount causes a rough surface of the thin film by forming titanium-based protrusions on the surface of the thin film (see, *Japanese Journal of Applied Physics*, 36, 6946 (1997)). Additionally, to apply the BST thin film to semiconductor devices such as DRAMS, the thin film must contain little or no impurities such as carbon. Also, to form a device structure, the thin film must be excellent in step coverage. However, multi-component metal oxide thin films deposited from the prior precursors are disadvantageous in that they are rough in their surface due to the use of an excess amount of the titanium precursor, they are high in their leakage current due to the presence of impurities such as carbon, etc., and they are inferior in their step coverage.

SUMMARY OF THE INVENTION

A feature of the present invention is a group IV metal precursor which exhibits excellent volatility, thermal stability and Chemical stability, and which is particularly suitable for use in the formation of multi-component metal oxide thin films containing a group IV metal such as titanium.

Another feature of the present invention is a chemical vapor deposition method using the group IV metal precursor.

In accordance with one aspect of the present invention, there is provided a tridentate ligand (L) having a charge of −2, which is represented by the following formula (I):

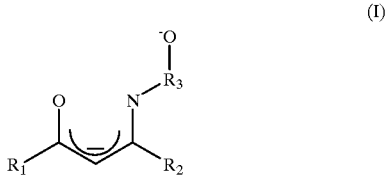

(I)

wherein each of $R_1$ and $R_2$, independently, is a linear or branched $C_{1-8}$ alkyl group; and $R_3$ is a linear or branched $C_{1-8}$ alkylene group.

In accordance with another aspect of the present invention, there is provided an organometallic precursor of the formula $M(L)_2$, for use in the formation of metal oxide thin films, in which M is a group IV metal ion having a charge of +4 and L is a tridentate ligand of the above formula (I) having a charge of −2.

In accordance with still another aspect of the present invention, there is provided a chemical vapor deposition method which comprises forming a metal oxide thin film using, as a group IV metal precursor, the organometallic precursor of the formula $M(L)_2$.

BRIEF DESCRIPTION OF THE DRAWINGS

The above and other objects and aspects of the present invention will be apparent from the following description of embodiments with reference to the accompanying drawings, in which.

DETAILED DESCRIPTION OF THE PREFERRED EMBODIMENTS

Figure 1A:
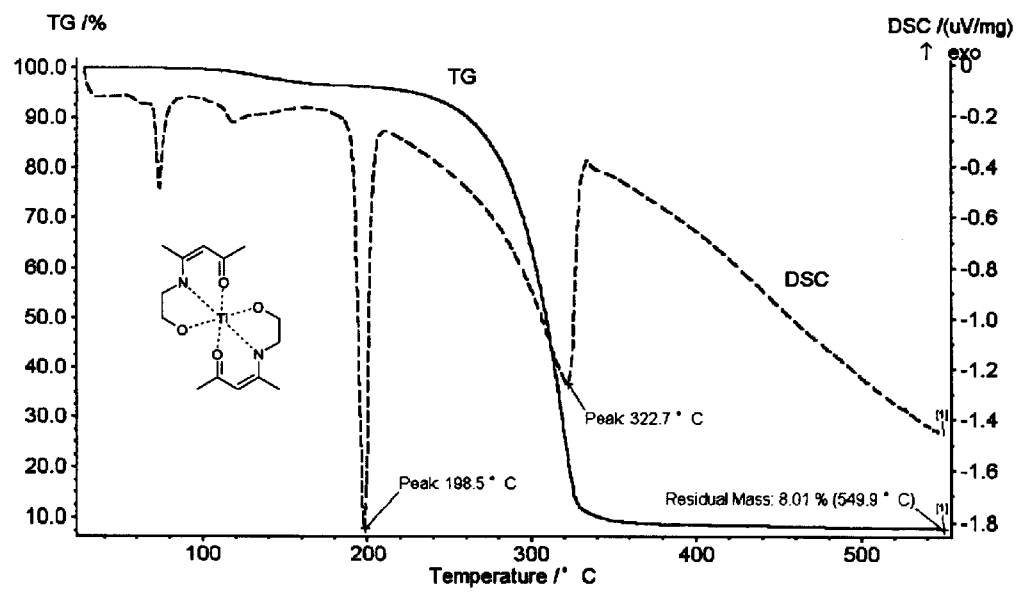
FIG. 1a is a plot of Thermal Gravimetry-Differential Scanning Calorimetry (TG-DSC) curves according to a temperature rise in nitrogen atmosphere for the precursor titanium bis[4-(ethoxy)imino-2-pentanoate] (Ti(eip)$_2$) of the present invention.
Figure 1B:
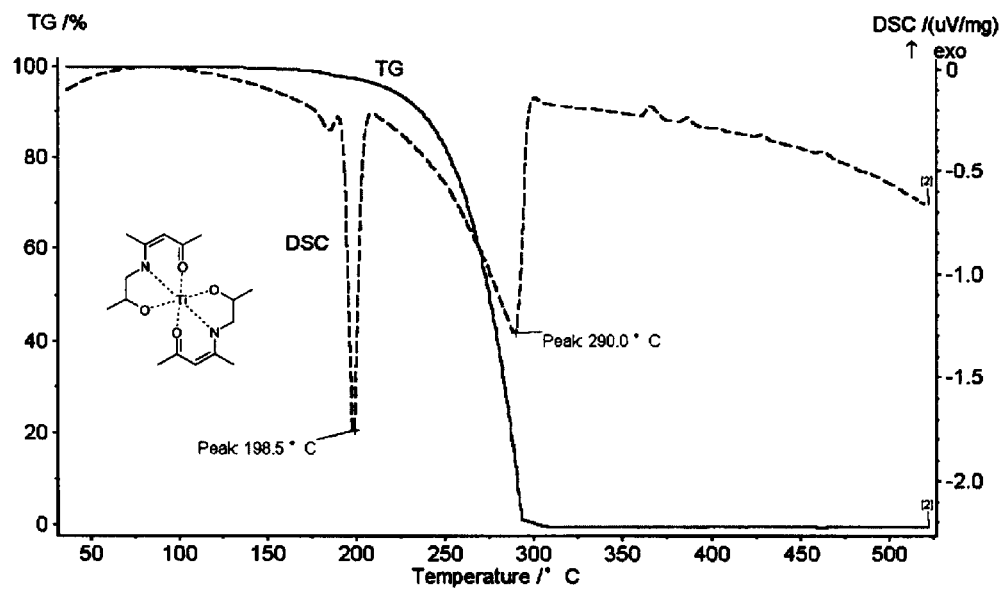
FIG. 1b is a plot of TG-DSC curves according to a temperature rise in nitrogen atmosphere for the precursor titanium bis[4-(2-methylethoxy)imino-2-pentanoate] (Ti(2meip)$_2$) of the present invention.
Figure 2A:
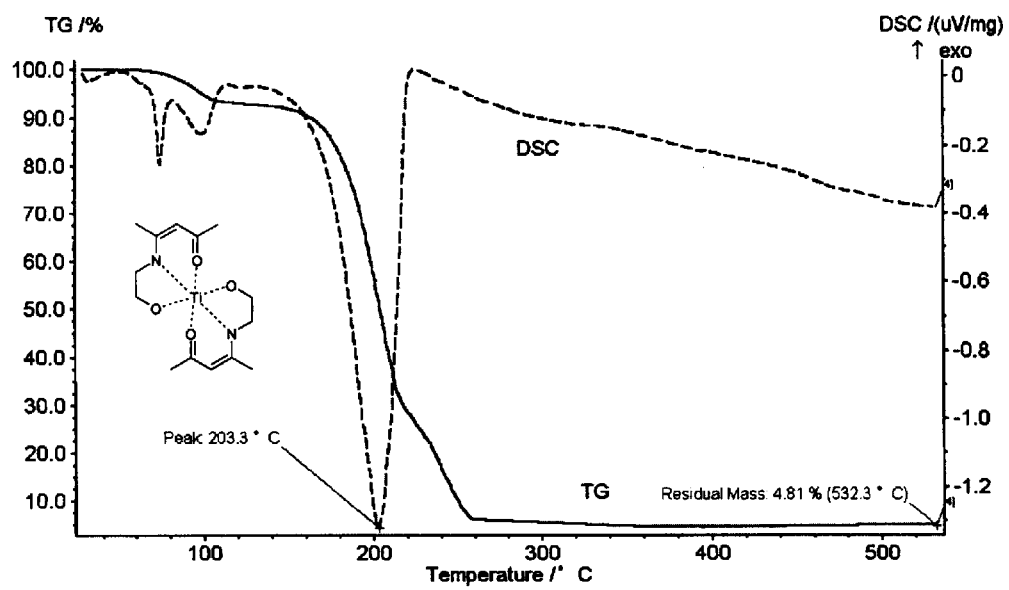
FIG. 2a is a plot of TG-DSC curves according to a temperature rise under a reduced pressure of about 1.3 mbar for the precursor Ti(eip)$_2$ of the present invention.
Figure 2B:
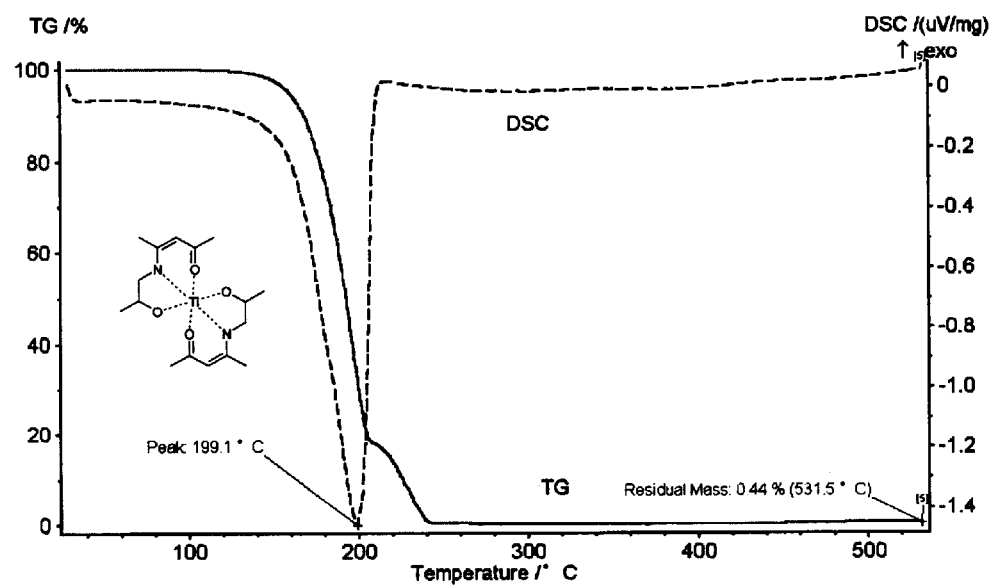
FIG. 2b is a plot of TG-DSC curves according to a temperature rise under a reduced pressure of about 1.3 mbar for the precursor Ti(2meip)$_2$ of the present invention.

The present invention provides a chemical vapor deposition method using, as a titanium precursor, titanium (N-alkoxy-β-ketoiminate)$_2$ which was previously reported as a catalyst in "*Organometallics*, 18, 1018 (1999)". Such a titanium precursor is saturated at the vacant coordination sites of the central titanium ion with two tridentate ligands which show much enhanced chelate effect over a bidentate ligand. Thus, this precursor is excellent in chemical stability and thermal properties, and does not leave residue after vaporization. Also, this precursor can be controlled with respect to its thermal properties, such as vaporization temperature, and residue amount after vaporization, etc. This allows the insurance of a similarity in vaporization and decomposition behaviors among metal precursors that are used in the deposition of a multi-component metal oxide thin film containing titanium. The ligand N-alkoxy-β-ketoiminate can be also applied to other group IV metal ions including Si, Zr, Hf, Ge, Sn and Pb in addition to Ti.

Briefly, the method of the present invention utilizes, as a group IV metal precursor, a complex represented by the formula $M(L)_2$ where M is a group IV metal ion and L is the ligand. The ligand (L) is characterized in that it is N-alkoxy-β-ketoiminate having a charge of −2 as indicated in the formula (I) below and is coordinated to a group IV metal ion having a charge of +4 as a tridentate ligand:

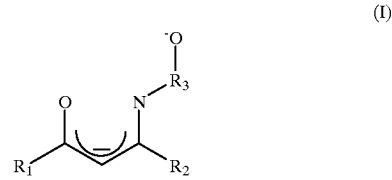

(I)

wherein each of $R_1$ and $R_2$, independently, is a linear or branched $C_{1-8}$ alkyl group; and $R_3$ is a linear or branched $C_{1-8}$ alkylene group. In particular, the $R_1$ and $R_2$ groups may be the same or different from one another to render the ligand (L) asymmetric.

To further improve the chelate effect of the ligand, the present invention introduces a linear or branched N-alkoxy group having a charge of −1 to a nitrogen atom of β-ketoiminate to convert the β-ketoiminate into a tridentate ligand having a charge of −2. The tridentate ligand thus prepared is strongly bound to a metal ion while saturating vacant coordination sites of the metal ion. Accordingly, the metal complex with the ligand (L) achieves excellent chemical and thermal stabilities.

Meanwhile, precursors of a formula $M(OR)_n$ and precursors of a formula $M(OR)_x(\beta\text{-diketonate})_y$ are generally converted into metal hydroxide complexes when being left to stand in air. In contrast, the precursors having the tridentate ligand according to the present invention, in particular the precursor $Ti(2meip)_2$ according to the following Example 12, have an excellent hydrolytic stability, as well as an excellent chemical stability in that they are not structurally changed even when left to stand in air for three months or more.

Since the group IV metal precursors according to the present invention are soluble in common organic solvents, such as benzene, toluene, chloroform, alcohol, tetrahydrofuran and n-butyl acetate, they can be used to form a thin film on a substrate by the Liquid Delivery MOCVD method. In particular, such precursors have an advantage in that its solubility in solvents such as n-butyl acetate commonly used in a Liquid Source Chemical Vapor Deposition (LSCVD) method may be increased by varying asymmetric moieties of the tridentate ligand.

The precursors according to the present invention exhibit highly improved thermal stability, are moisture proof and exhibit chemical stability. These properties are significantly dependent on the asymmetry of the ligand, as well as the kinds of groups $R_1$, $R_2$ and $R_3$. In the case of the precursor $Ti(epi)_2$ where the tridentate ligand does not contain any asymmetric moiety, it leaves a residue of about 8% after evaporation. In contrast, the precursors $Ti(2meip)_2$ and $Ti(22dm2meih)_2$ (titanium bis[2,2-dimethyl-5-(2-methylethoxy) imino-3-heptanonate]), respectively, are melted at 198° C. and 218° C. under atmospheric pressure and then rapidly vaporized at 290° C. and 287° C. without being thermally decomposed. It can be thus found that the precursors $Ti(2meip)_2$ and $Ti(22dm2meih)_2$ possess excellent thermal properties in that they leave no residues after being vaporized.

In depositing a multi-component thin film by the chemical vapor deposition (CVD) method, metal precursors used are generally different in their vaporization temperature from each other and are not similar in their decomposition behavior. For this reason, supplying excess metal precursor of a relatively high volatility is necessary to control the metal composition of the thin film. Accordingly, in the deposition of multi-component thin film, the use of a combination of precursors having similar volatility and decomposition behaviors is highly critical to form a thin film having a good quality. In particular, precursors having a small charge-to-radius ratio, such as Ba, Sr and the like, are not sufficiently coordinated with ligands at their coordination sites. Thus, the precursors having such metals are higher in vaporization temperature by at least 100° C. compared to the titanium precursor, as indicated in Table 2. However, while the precursors according to the present invention are vaporized at a higher temperature than that of the prior titanium precursors, they leave no residues after vaporization and are completely decomposed above a certain temperature on thermal decomposition in an oxygen atmosphere. Thus, the precursors according to the present invention are particularly useful in forming a multi-component thin film with metals of a low volatility. In addition, the precursors of the present invention enable the formation of a high quality-thin film which has a smooth surface and excellent step coverage, and which contains little or no impurities, such as carbon or nitrogen, etc.

Meanwhile, in depositing the multi-component thin film such as BST on a large area substrate, the temperature of the substrate is not maintained uniformly throughout the substrate. Moreover, in fabricating a device with a high aspect ratio, the higher and lower topology portions of the device are not maintained at the same temperature. For these reasons, it was difficult for the prior methods to maintain the titanium content at the same level throughout the large area substrate or the upper and lower portions of the high topology thin film. In contrast, for the titanium precursor according to the present invention, the temperature dependence of the titanium content in thin film is low as compared to that for the prior titanium precursors. This provides easy control of the metal composition in the large area thin film and the high topology thin film.

The following examples are for further illustration purposes only and in no way limit the scope of this invention.

EXAMPLE 1

Preparation of $CH_3C(O)CHC(HNCH_2CH_2OH)CH_3$

As described in *Organometallics*, 18, 1018 (1999), 6.71 g (109.8 mmol) of ethanol amine of a formula $NH_2CH_2CH_2OH$ and 10 g (99.88 mmol) of 2,4-pentanedione of a formula $CH_3C(O)CH_2C(O)CH_3$, as starting materials, were mixed with 120 ml of $CH_2Cl_2$, and stirred for one day at room temperature. Then, the resulting material was extracted with a mixed solution of $H_2O/CH_2Cl_2$ (15 ml/150 ml) into an organic layer, and the remaining water layer was further extracted three times with 100 ml of a $CH_2Cl_2$ solution. After drying the collected organic solution in the presence of $MgSO_4$, the solvent was removed from the solution, and $CH_2Cl_2$/n-hexane (10 ml/140 ml) was added. As a result, the mixture was recrystallized at −20° C. to give 12.88 g (90% yield) of $CH_3C(O)CHC(HNCH_2CH_2OH)CH_3$.

EXAMPLE 2

Preparation of $CH_3C(O)CHC(HNCH_2CH(CH_3)OH)CH_3$

The same procedure as in Example 1 was carried out to give 29.38 g (95% yield) of $CH_3C(O)CHC(HNCH_2CH(CH_3)OH)CH_3$, except that 22.51 g (299.7 mmol) of 1-amino-2-propanol of a formula $NH_2CH_2CH(CH_3)OH$ and 20 g (199.8 mmol) of 2,4-pentanedion were used as the starting materials.

EXAMPLE 3

Preparation of $CH_3C(O)CHC(HNCH(CH_3)CH_2OH)CH_3$ 10.0 g (13.31 mmol) of DL-2-amino-1-propanol of a formula $NH_2CH(CH_3)CHOH$ and 11.11 g (11.10 mmol) of 2,4-pentanedione were mixed with 100 ml of $CH_3OH$, to which 0.51 g of HCOOH was added. The mixture was refluxed for one day at 85° C. while stirring. After removing the solvent, the resulting material was extracted with a mixed solution of $H_2O/CH_2Cl_2$ (20 ml/150 ml) into an organic layer, and the remaining water layer was further extracted three times with 100 ml of a $CH_2Cl_2$ solution. After drying the collected organic solution in the presence Of $MgSO_4$, the solvent was removed from the solution. The remaining material was purified through a column filled with silica, using ethyl acetate as a developing solution, to give 15.52 g (89% yield) of $CH_3C(O)CHC(HNCH(CH_3)CH_2OH)CH_3$.

NMR results measured for the product are as follows:
$^1$H-NMR (199.976 MHz, $CDCl_3$): 10.8(br s, 1H, C(O)CH=C(NH)), 4.93(s, 1H, C(O)CH=C(NH)), 3.72(m, 1H, HNCH(Me)CH$_2$OH), 3.62(dd, 1H, NCHMeCH$_a$H$_b$OH), 3.52(dd, 1H, NCHMeCH$_a$H$_b$OH), 3.35(br s, 1H, NCH(Me)CH$_2$OH), 1.98(s, 3H, CH=C(NH)CH$_3$), 1.97(s, 3H, CH$_3$C(O)CH), 1.18(d, 3H, HNCH(CH$_3$)CH$_2$OH); $^{13}$C-NMR (50.289 MHz, $CDCl_3$): 192.45(s, CH$_3$C(O)CH), 160.69(s, CH=C(NH)CH$_3$), 93.19(s, C(O)CH=C(NH), 64.57(s, HNCH(Me)CH$_2$OH), 48.45(s, HNCH(Me)CH$_2$OH), 26.19 (s, CH$_3$C(O)CH), 16.69(s, CH=C(NH)CH$_3$), 15.7(s, NHCH(CH$_3$)CH$_2$OH).

EXAMPLE 4

Preparation of $CH_3C(O)CHC(HNC(CH_3)_2CH_2OH)CH_3$ 13.35 g (149.8 mmol) of 2-amino-2-methyl-1-propanol of a formula $NH_2C(CH_3)_2CHOH$ and 10.0 g (99.88 mmol) of 2,4-pentanedione, as starting materials, were mixed with 100 ml of $CH_3OH$, to which 0.51 g of HCOOH was added. The mixture was refluxed for one day at 85° C. while stirring. After removing the solvent, the remaining material was recrystallized from ethyl ether at room temperature to give 10.95 g (64% yield) of $CH_3C(O)CHC(HNC(CH_3)_2CH_2OH)CH_3$.

NMR results measured for the product are as follows:
$^1$H-NMR (199.976 MHz, $CDCl_3$): 11.32(br s, 1H, C(O)CH=C(NH)), 4.88(s, 1H, C(O)CH=C(NH)), 4.35(br s, 1H, HNC(Me)$_2$CH$_2$OH), 3.53(s, 2H, NC(Me)$_2$CH$_2$OH), 2.04(s, 3H, CH=C(N)CH$_3$), 1.94(s, 3H, CH$_3$C(O)), 1.33(s, 6H, (HNC(CH$_3$)$_2$CH$_2$OH); $^{13}$C-NMR (50.289 MHz, $CDCl_3$): 194.24(s, CH$_3$C(O)CH), 163.88(s, CH=C(NH)CH$_3$), 97.07 (s, C(O)CH=(NH)), 70.93(s, NHC(Me)$_2$CH$_2$OH), 56.44(s, HNC(Me)$_2$CH$_2$OH), 28.67(s, CH=C(NH)CH$_3$), 25.72(s, HNC(CH$_3$)$_2$CH$_2$OH), 20.96(s, CH$_3$C(O)CH); EA (cal C: 63.13, H: 10.01, N: 8.18, found C: 63.38, H: 10.57, N: 8.23)

EXAMPLE 5

Preparation of $CH_3C(O)CHC(HNCH(CH_2CH_3)CH_2OH)CH_3$

The same procedure as in Example 3 was carried out, except that 13.35 g (149.8 mmol) of 2-amino-1-butanol and 10.0 g (99.88 mmol) of 2,4-pentanedion, as the starting materials, were mixed with 100 ml of $C_2H_5OH$. The product was finally purified through vacuum distillation to give 14.54 g (85% yield) of $CH_3C(O)CHC(HNCH(CH_2CH_3)CH_2OH)CH_3$ as a yellowish liquid.

NMR results measured for the product are as follows:
$^1$H-NMR (199.976 MHz, $CDCl_3$): 10.74(br s, 1H, C(O)CH=C(NH)), 4.94 (s, 1H, C(O)CH=C(NH)), 4.06(d, 2H, NCH(CH$_2$CH$_3$)CH$_2$OH), 3.60(m, 1H, NCH(CH$_2$CH$_3$)CH$_2$OH), 3.25(br s, 1H, HNCH(CH$_2$CH$_3$)CH$_2$OH), 1.99(s, 3H, CH=C(N)CH$_3$), 1.93(s, 3H, CH$_3$C(O)), 1.59(m, 2H, (HNCH(CH$_2$CH$_3$)CH$_2$OH), 0.95(t, 3H, HNCH(CH$_2$CH$_3$)CH$_2$OH); $^{13}$C-NMR (50.289 MHz, $CDCl_3$): 195.15(s, CH$_3$C(O)CH), 163.86(s, CH=C(NH)CH$_3$), 95.87(s, C(O)CH=C(NH)), 65.91(s, HNCH(CH$_2$CH$_3$)CH$_2$OH), 57.23(s, HNCH(CH$_2$CH$_3$)CH$_2$OH), 28.90(s, CH$_3$C(O)CH), 25.54(s, HNCH(CH$_2$CH$_3$)CH$_2$OH), 19.66(s, CH=C(NH)CH$_3$), 10.56(s, NHCH(CH$_2$CH$_3$)CH$_2$OH).

EXAMPLE 6

Preparation of $CH_3C(O)CHC(HNCH_2CH_2CH_2OH)CH_3$

The same procedure as in Example 1 was carried out, except that 9.0 g (119.8 mmol) of 3-amino-1-propanol and 10.0 g (99.88 mmol) of 2,4-pentanedion were used as the starting materials. The product was finally purified through a column filled with silica, using a mixed solution of ethyl acetate/hexane as a developing solution, to give 14.00 g (93% yield) of $CH_3C(O)CHC(HNCH_2CH_2CH_2OH)CH_3$.

NMR results measured for the product are as follows:
$^1$H-NMR (199.976 MHz, $CDCl_3$): 10.86(br s, 1H, C(O)CH=C(NH)), 4.96(s, 1H, C(O)CH=C(NH)), 3.74(t, 2H, NCH$_2$CH$_2$CH$_2$OH), 3.38(dt, 2H, NCH$_2$CH$_2$CH$_2$OH), 2.67 (br s, 1H, NCH$_2$CH$_2$CH$_2$OH), 1.98(s, 3H, CH=C(NH)CH$_3$), 1.94(s, 3H, CH$_3$C(O)CH), 1.83(m, 2H, NCH$_2$CH$_2$CH$_2$OH); $^{13}$C-NMR (50.289 MHz, $CDCl_3$): 194.94 (s, CH$_3$C(O)CH), 163.80 (s, CH=C(NH)CH$_3$), 95.46(s, C(O)CH=C(NH)), 59.62(s, HNCH$_2$CH$_2$CH$_2$OH), 39.92(s, HNCH$_2$CH$_2$CH$_2$OH), 32.85(s, HNCH$_2$CH$_2$CH$_2$OH), 28.85(s, CH$_3$C(O)CH), 18.99 (s, CH=C(NH)CH$_3$).

EXAMPLE 7

Preparation of $(CH_3)_2CHC(O)CHC(HNCH_2CH(CH_3)OH)(CH(CH_3)_2)$ 5.77 g (76.8 mmol) of 1-amino-2-propanol of a formula $NH_2CH_2CH(CH_3)OH$ and 10.0 g (64.0 mmol) of 2,6-dimethyl-3,5-heptanedione of a formula $(CH_3)_2CHC(O)CH_2C(O)(CH(CH_3)_2)$ were mixed with 180 ml of a benzene solution, to which 0.63 g (1 drop) of $H_2SO_4$ or HCOOH was added. The mixture was refluxed for 6 hours at 110° C. with stirring, and $H_2O$ was collected through a Dean-Stark device. The remaining material was extracted with a mixed solution of $H_2O$/benzene (20 ml/250 ml) into an organic layer, and the remaining water layer was further extracted three times with 100 ml of a benzene solution. After drying the collected organic solution in the presence of $MgSO_4$, the solvent was removed from the solution, and 100 ml of n-hexane was added. The mixture was recrystallized at −20° C. to give 11.61 g (85% yield) of $(CH_3)_2CHC(O)CHC(HNCH_2CH(CH_3)OH)(CH(CH_3)_2)$ NMR results measured for the product are as follows:
$^1$H NMR ($CDCl_3$): 11.21 (br s, 1H, C(O)CH=CNH), 5.01 (s, 1H, C(O)CH=CNH), 3.95 (q, 1H, HNCH$_2$CHMeOH), 3.42 (br s, 1H, NCH$_2$CH$_2$OH), 3.22 (m, 2H, HNCH$_2$CHMeOH), 2.70 (h, 1H, HNCCHMe$_2$), 2.42 (h, 1H, Me$_2$CHC(O)CH), 1.23 (d, 3H, NCH$_2$CH(CH$_3$)OH), 1.10 (d, 6H, HNCCH(CH$_3$)$_2$), 1.05 (d, 6H, (CH$_3$)$_2$CHC(O)CH); $^{13}$C NMR ($CDCl_3$): 200.82 (s, Me$_2$CHC(O)CH), 171.90 (s, HNCCHMe$_2$), 86.42 (s, C(O)CH=CN), 65.13 (s, NCH$_2$CHMeOH), 47.92 (s, HNCH$_2$CHMeOH), 38.12 (s, Me$_2$CHC(O)CH), 26.85 (s, HNCCHMe$_2$), 19.56 (s, HNCCH(C$_a$H$_3$)(C$_b$H$_3$)), 19.47 (s, HNCCH(C$_a$H$_3$)(C$_b$H$_3$)), 19.20 (s, NCH$_2$CH(CH$_3$)OH), 18.27 (s, (CH$_3$)$_2$CHC(O)CH), EA(cal C: 67.57, H: 10.87, N: 6.56, Found C: 67.44, H: 11.33, N: 6.48).

EXAMPLE 8

Preparation of $(CH_3)_2CHC(O)CHC(HNCH(CH_3)CH_2OH)(CH(CH_3)_2)$

The same procedure as in Example 7 was carried out to give 11.65 g (81% yield) of $(CH_3)_2CHC(O)CHC(HNCH(CH_3)CH_2OH)(CH(CH_3)_2)$, except that 7.21 g (95.99 mmol) of DL-2-amino-1-propanol and 10.0 g (64.0 mmol) of 2,6-dimethyl-3,5-heptanedion were used as the starting materials.

NMR results measured for the product are as follows:
$^1$H-NMR (199.976 MHz, $CDCl_3$): 11.12(br d, 1H, C(O)CH=C(NHCH(Me))), 5.03(s, 1H, C(O)CH=C(NH)), 3.79 (m, 1H, HNCH(Me)CH$_2$OH), 3.59(br m, 2H, NCHMeCH$_2$OH), 2.89(br s, 1H, NCH(Me)CH$_2$OH), 2.78 (m, 1H, CH=C(NH)CH(CH$_3$)$_2$), 2.45(m, 1H, (CH$_3$)$_2$CHC(O)CH), 1.22(d, 3H, NCH(CH$_3$)CH$_2$OH), 1.15(d, 6H, CH=C(N)CH(CH$_3$)$_2$), 1.07 (dd, 6H (CH$_3$)$_2$CHC(O)); $^{13}$C NMR (CDCl$_3$): 202.57 (s, Me$_2$CHC(O)CH), 173.73 (s, HNCCHMe$_2$), 88.24 (s, C(O)CH=CN), 67.28 (s, NCH(Me) CH$_2$OH), 50.00 (s, HNCH(Me)CH$_2$OH), 39.93 (s, Me$_2$CHC (O)CH), 28.75 (s, HNCCHMe$_2$), 22.03 (s, HNCCH(C$_a$H$_3$) (C$_b$H$_3$)), 21.72 (s, HNCCH(C$_a$H$_3$)(C$_b$H$_3$)), 20.16 (s, (CH$_3$)$_2$ CHC(O)CH) 18.90 (s, NCH(CH$_3$)CH$_2$OH); EA(cal C: 67.57, H: 10.87, N: 6.57. Found C: 67.44, H: 11.70, N: 6.52).

EXAMPLE 9
Preparation of (CH$_3$)$_3$CC(O)CHC(HNCH$_2$CH$_2$OH)CH$_3$

The same procedure as in Example 7 was carried out to give 9.40 g (89% yield) of (CH$_3$)$_3$CC(O)CHC (HNCH$_2$CH$_2$OH)CH$_3$, except that 9.73 g (68.44 mmol) of ethanol amine and 8.11 g (57.03 mmol) of 2,2-dimethyl-3,5-hexanedion were used as the starting materials.

NMR results measured for the product are as follows:
$^1$H NMR (CDCl$_3$): 11.04 (br s, 1H, C(O)CH=CNH), 5.14 (s, 1H, C(O)CH=CNH), 3.76 (t, 2H, HNCH$_2$CH$_2$OH), 3.39 (dt, 1H, HNCH$_2$CH$_2$OH), 3.11 (br s, 1H, HNCH$_2$CH$_2$OH), 1.97 (s, 3H, HNCCH$_3$), 1.11(s, 9H, (CH$_3$)$_3$CC(O)CH); $^{13}$C NMR (CDCl$_3$): 202.39 (s, Me$_3$CC (O)CH), 162.54 (s, HNCCH$_3$), 89.32 (s, C(O)CH=CNH), 60.02 (s, NCH$_2$CH$_2$OH), 43.63 (s, HNCH$_2$CH$_2$OH), 39.58 (s, (CH$_3$)$_3$CC(O)CH), 26.25 (s, (CH$_3$)$_3$CC(O)CH), 17.82 (s, HNCCH$_3$); EA(cal C: 64.83, H: 10.34, N: 7.56. Found C: 64.76, H: 10.82, N: 7.60).

EXAMPLE 10
Preparation of (CH$_3$)$_3$CC(O)CHC(HNCH$_2$CH(CH$_3$)OH) CH$_3$

The same procedure as in Example 3 was carried out, except that 6.34 g (84.38 mmol) of 1-amino-2-propanol and 10.00 g (70.32 mmol) of 2,2-dimethyl-3,5-hexanedion, as the starting materials, were mixed with C$_2$H$_5$OH. The product was recrystallized from n-hexane at −20° C. to give 10.93 g (78% yield) of (CH$_3$)$_3$CC(O)CHC(HNCH$_2$CH (CH$_3$)OH)CH$_3$.

NMR results measured for the product are as follows:
$^1$H NMR (CDCl$_3$): 11.04 (br s, 1H, C(O)CH=CNH), 5.13 (s, 1H, C(O)CH=CNH), 3.96 (m, 1H, HNCH$_2$CH(Me) OH), 3.26 (dd, 1H, HNCH$_a$H$_b$CH(Me)OH), 3.20 (dd, 1H, HNCH$_a$H$_b$CH(Me)OH), 3.19 (br s, 1H, HNCH$_2$CH(Me) OH), 1.96 (s, 3H, HNCCH$_3$), 1.23(d, 3H, HNCH$_2$CH(CH$_3$) OH), 1.11(s, 9H, (CH$_3$)$_3$CC(O)CH); $^{13}$C NMR (CDCl$_3$): 204.16 (s, Me$_3$CC(O)CH), 164.20 (s, HNCCH$_3$), 91.18 (s, C(O)CH=CNH), 67.11 (s, NCH$_2$CH(Me)OH), 50.71 (s, HNCH$_2$CH(Me)OH), 41.46(s, (CH$_3$)$_3$CC(O)CH), 28.16(s, (CH$_3$)$_3$CC(O)CH), 21.00 (s, HNCCH$_3$), 19.77 (s, HNCH$_2$CH(CH$_3$)OH); EA (cal C: 66.29, H: 10.62, N: 7.03, found C: 65.72, H: 11.08, N: 7.12).

EXAMPLE 11
Preparation of Ti(CH$_3$C(O)CHC(NCH$_2$CH$_2$O)CH$_3$)$_2$, Ti(eip)$_2$ 3.67 g (25.61 mmol) of the tridentate ligand of a formula CH$_3$C(O)CHC(CH$_3$)(HNCH$_2$CH$_2$OH) prepared in Example 1 was dissolved in 20 ml of methylene dichloride. To this solution, a solution of 3.31 g (11.64 mmol) of titanium (isopropoxide)$_4$, Ti(O-iPr)$_4$, in 25 ml of methylene dichloride was added through a cannular at room temperature with stirring. The mixed yellowish solution was stirred for 4 hours or more, after which the solvent was removed under a reduced pressure. The remaining material was recrystallized from a mixed solution of methylene dichloride and n-hexane at −20° C. to give 3.72 g (95% yield) of Ti(CH$_3$C (O)CHC(NCH$_2$CH$_2$O)CH$_3$)$_2$ as a pure yellow solid.

EXAMPLE 12
Preparation of Ti(CH$_3$C(O)CHC(NCH$_2$CHMeO)CH$_3$)$_2$, Ti(2meip)$_2$ This Example was carried out according to the same procedure as in Example 11, using 11.06 g (70.36 mmol) of CH$_3$C(O)CHC(CH$_3$)(HNCH$_2$CH(Me)OH) prepared in Example 2 and 10.0 g (35.18 mmol) of Ti(O-iPr)$_4$. Thus, 12.18 g (96% yield) of Ti(CH$_3$C(O)CHC(NCH$_2$CHMeO) CH$_3$)$_2$ was obtained.

EXAMPLE 13
Preparation of Ti(CH$_3$C(O)CHC(NCHMeCH$_2$O)CH$_3$)$_2$, Ti(1meip)$_2$ This Example was carried out according to the same procedure as in Example 11, using 8.0 g (50.89 mmol) of CH$_3$C(O)CH$_2$C(CH$_3$)(NCHMeCH$_2$OH) prepared in Example 3 and 7.23 g (25.44 mmol) of Ti(O-iPr)$_4$. Thus, 8.38 g (92% yield) of Ti(CH$_3$C(O)CHC(NCHMeCH$_2$O) CH$_3$)$_2$ was obtained.

NMR results measured for the product are as follows:
$^1$H-NMR (199.976 MHz, CDCl$_3$) 5.27, 5.24, 5.08, 5.08 (s 2H, C(O)CHC(N)), 4.79 (dd, 1H, NCH(Me)CH$_{ab}$H$_{cd}$O), 4.58(dd, 1H, NCH(Me)CH$_{ab}$H$_{cd}$O), 4.35 (m, 2H, NCH(Me) CH$_2$O), 4.00(dd, 1H, NCH(Me)CH$_{ab}$H$_{cd}$O), 3.83(dd, 1H, NCH(Me)CH$_{ab}$H$_{cd}$O), 2.14, 2.12, 2.11, 2.07(s, 6H, C(N) CH$_3$), 1.94, 1.92, 1.88, 1.80(s, 6H, CH$_3$C(O)), 1.51, 1.37, 1.32, 1.24, 1.17(d, 6H, NCH(CH$_3$)CH$_2$O); $^{13}$C-NMR (50.289 MHz, CDCl$_3$) 176.72, 175.83, 175.40(s, CH$_3$C(O)), 167.89, 167.27, 166.76(s, C(N)CH$_3$), 103.30, 103.20, 102.01(s, C(O)CHC(N)), 78.07, 78.00, 77.14(s, NCH(Me) CH$_2$O), 66.14, 65.73, 65.24, 64.96(s, NCH(Me)CH$_2$O), 24.92, 24.58, 24.40, 24.25(CH$_3$C(O)), 21.82, 21.59, 21.43, 20.74(C(N)CH3), 20.35, 20.08, 19.30, 18.35(NCH(CH$_3$) CH$_2$O); EA (cal C: 53.64, H: 7.32, N: 7.82, found C: 53.32, H: 7.66, N: 7.79)

EXAMPLE 14
Preparation of Ti(CH$_3$C(O)CHC(NC(Me)$_2$CH$_2$O)CH$_3$)$_2$, Ti(1deip)$_2$ This Example was carried out according to the same procedure as in Example 11, using 3.01 g (17.58 mmol) of CH$_3$C(O)CHC(CH$_3$)(HNC(Me)$_2$CH$_2$OH) prepared in Example 4 and 2.50 g (8.79 mmol) of Ti(O-iPr)$_4$. Thus, 3.19 g (94% yield) of Ti(CH$_3$C(O)CHC(NC(Me)$_2$CH$_2$O)CH$_3$)$_2$ was obtained.

NMR results measured for the product are as follows:
$^1$H-NMR (199.976 MHz, CDCl$_3$) 5.13 (s, 2H, C(O)CHC (N)), 4.32 (d, 2H, NC(Me)$_2$CH$_a$H$_b$O), 4.01 (d, 2H, NC(Me)$_2$ CH$_a$H$_b$O), 2.21(s, 6H, C(N)CH$_3$), 1.92 (s, 6H, CH$_3$C(O)), 1.56 (s, 6H, NC(CH$_3$)$_a$(CH$_3$)$_b$CH$_2$O), 1.38 (s, 6H, NC (CH$_3$)$_a$(CH$_3$)$_b$CH$_2$O); $^{13}$C-NMR (50.289 MHz, CDCl$_3$) 174.70(s, CH$_3$C(O)), 169.31(s, C(N)CH$_3$), 104.71(s, C(O) CHC(N)), 84.79(s, NC(Me)$_2$CH$_2$O), 71.41(s, NC(Me)$_2$ CH$_2$O), 25.69(s, CH$_3$C(O)), 25.1(s, C(N)CH$_3$), 24.5(s, NCC$_a$H$_3$C$_b$H$_3$CH$_2$O), 24.4(s, NCC$_a$H$_3$C$_b$H$_3$CH$_2$O); EA (cal C: 55.96, H: 7.83, N: 7.25, found C: 55.59, H: 8.22, N: 6.87).

EXAMPLE 15
Preparation of Ti(CH$_3$C(O)CHC(NCH(CH$_2$CH$_3$)CH$_2$O) CH$_3$)$_2$, Ti(1eeip)$_2$ This Example was carried out according to the same procedure as in Example 11, using 2.30 g (13.44 mmol) of CH$_3$C(O)CHC(HNCH(CH$_2$CH$_3$)CH$_2$O)CH$_3$ prepared in Example 5 and 1.91 g (6.72 mmol) of Ti(O-iPr)$_4$. Thus, 2.41 g (93% yield) of Ti(CH$_3$C(O)CHC(NCH(CH$_2$CH$_3$)CH$_2$O) CH$_3$)$_2$ was obtained.

NMR results measured for the product are as follows:
$^1$H-NMR (199.976 MHz, CDCl$_3$) 5.28, 5.25, 5.09 (s, 2H, C(O)CHC(N)), 4.70 (dd, 1H, NCH(CH$_2$CH$_3$)CH$_{ab}$H$_{cd}$O), 4.65(dd, 1H, NCH(CH$_2$CH$_3$)CH$_{ab}$H$_{cd}$O), 4.18(dd, 1H, NCH(CH$_2$CH$_3$)CH$_{ab}$H$_{cd}$O), 4.17(dd, 1H, NCH(CH$_2$CH$_3$)CH$_{ab}$H$_{cd}$O), 4.03 (m, 2H, NCH(CH$_2$CH$_3$)CH$_2$O), 2.29–2.14(m, 2H, NCH(CH$_2$CH$_3$)CH$_2$O), 2.11, 2.06 (s, 6H, C(N)CH$_3$), 1.92, 1.89, 1.80(s, 6H, CH$_3$C(O)), 1.72–1.55(m, 2H, NCH(CH$_2$CH$_3$)CH$_2$O), 0.97(t, 6H, NCH(CH$_2$CH$_3$)CH$_2$O); $^{13}$C-NMR (50.289 MHz, CDCl$_3$) 175.89, (s, CH$_3$C(O)), 167.13(s, C(N)CH$_3$), 102.04(s, C(O)CHC(N)), 74.46 (s, NCH(CH$_2$CH$_3$)CH$_2$O) 72.78(s, NCH(CH$_2$CH$_3$)CH$_2$O), 24.48(s, NCH(CH$_2$CH$_3$)CH$_2$O), 24.67(CH$_3$C(O)), 21.99(C(N)CH$_3$), 11.77(NCH(CH$_2$CH$_3$)CH$_2$O); EA (cal C: 55.96, H: 7.83, N: 7.25 found C: 55.85, H: 8.30, N: 7.34).

EXAMPLE 16

Preparation of Ti(CH$_3$C(O)CHC(NCH$_2$CH$_2$CH$_2$O) CH$_3$)$_2$, Ti(pip)$_2$

This Example was carried out according to the same procedure as in Example 11, using 1.11 g (7.04 mmol) of CH$_3$C(O)CHC(HNCH$_2$CH$_2$CH$_2$O)CH$_3$ prepared in Example 6 and 1.0 g (3.52 mmol) of Ti(O-iPr)$_4$. Thus, 1.20 g (95.24% yield) of Ti(CH$_3$C(O)CHC(NC(Me)$_2$CH$_2$O)CH$_3$)$_2$ was obtained.

NMR results measured for the product are as follows:
$^1$H-NMR (199.976 MHz, CDCl$_3$) 5.14(s, 2H, C(O)CHC(N)), 4.36(t, 4H, NCH$_2$CH$_2$CH$_2$O), 3.64(t, 4H, NCH$_2$CH$_2$CH$_2$O), 2.07(m, 4H, NCH$_2$CH$_2$CH$_2$O), 2.00(s, 6H, C(N)CH$_3$), 1.90(s, 6H, CH$_3$C(O); $^{13}$C-NMR (50.289 MHz, CDCl$_3$) 176.05(s, CH$_3$C(O)), 168.01(s, C(N)CH$_3$), 103.64(s, C(O)CHC(N)), 73.23(s, NCH$_2$CH$_2$CH$_2$O), 50.19 (s, NCH$_2$CH$_2$CH$_2$O), 32.34(s, NCH$_2$CH$_2$CH$_2$O), 25.33(s, CH$_3$C(O)), 22.41(s, C(N)CH$_3$).

EXAMPLE 17

Preparation of Ti((CH$_3$)$_2$CHC(O)CHC(CH(CH$_3$)$_2$)(NCH$_2$CH(Me)C)$_2$)$_2$, Ti(26dm2meih)$_2$ This Example was carried out according to the same procedure as in Example 11, using 1.5 g (7.03 mmol) of (CH$_3$)$_2$CHC(O)CHC(CH(CH$_3$)$_2$)(HNCH$_2$CH(Me)OH) prepared in Example 7 and 1.0 g (3.52 mmol) of Ti(O-iPr)$_4$. Thus, 1.57 g (95% yield) of Ti((CH$_3$)$_2$CHC(O)CHC(NCH$_2$CH(Me)O)CH(CH$_3$)$_2$)$_2$ was obtained.

NMR results measured for the product are as follows:
$^1$H-NMR (199.976 MHz, CDCl$_3$) 5.23, 5.22, 5.20, 5.15 (s, 2H, C(O)CHC(N)), 4.87(m, 2H, NCH$_2$CHMeO), 4.22(dd, 1H, NCH$_{ab}$H$_{cd}$CH(Me)O), 4.13(dd, 1H, NCH$_{ab}$H$_{cd}$CH(Me)O), 3.88(dd, 1H, NCH$_{ab}$H$_{cd}$CH(Me)O), 3.76(dd, 1H, NCH$_{ab}$H$_{cd}$CH(Me)O), 2.92(m, 2H, C(N)CH(Me)$_2$), 2.30(m, 2H, CH(Me)$_2$C(O)), 1.11–1.23(d*4, 12H, C(N)CH(CH$_3$)$_2$), 1.21(d*3, 6H, NCH$_2$CH(CH$_3$)O), 0.88–0.98 (d*4, 12H, (CH$_3$)$_2$CHC(O)); $^{13}$C-NMR (50.289 MHz, CD$_2$Cl$_2$) 183.51, 183.35, 183.02(s, (CH$_3$)$_2$CHC(O)), 177.05, 176.49, 175.91, 175.70(s, C(N)(CH(CH$_3$)$_2$)), 93.46, 93.30, 93.19(s, C(O)CHC(N)), 76.99, 76.52, 76.40, 76.12(s, NCH$_2$CH(Me)O), 65.96, 65.60, 64.79(s, NCH$_2$CH(Me)O), 36.35, 36.27, 36.13 (s, (CH$_3$)$_2$CHC(O)), 31.46, 31.40, 31.24(s, C(N)(CH(CH$_3$)$_2$)), 21.66–20.18 (d, (CH$_3$)$_2$CHC(O)CHC(NCH$_2$CH(CH$_3$)O)(CH(CH$_3$)$_2$))

EXAMPLE 18

Preparation of Ti((CH$_3$)$_2$CHC(O)CHC(NCH(Me)CH$_2$O)CH(CH$_3$)$_2$)$_2$, Ti(26dm1meih)$_2$ This Example was carried out according to the same procedure as in Example 11, using 6.0 g (28.14 mmol) of (CH$_3$)$_2$CHC(O)CH$_2$C(CH(CH$_3$)$_2$)(NCH(Me)CH$_2$OH) prepared in Example 8 and 4.0 g (14.07 mmol) of Ti(O-iPr)$_4$. Thus, 6.22 g (93.96% yield) of Ti((CH$_3$)$_2$CHC(O)CHC(NCH(Me)CH$_2$O)CH(CH$_3$)$_2$)$_2$ was obtained.

NMR results measured for the product are as follows:
$^1$H-NMR (199.976 MHz, CDCl$_3$) 5.34, 5.17, 5.13(s, 2H, C(O)CHC(N)), 4.83(dd, 1H, NCH(Me)CH$_{ab}$H$_{cd}$O), 4.79 (dd, 1H, NCH(Me)CH$_{ab}$H$_{cd}$O), 4.56(m, 1H, NCH$_a$(Me)CH$_2$O), 4.38(m, 1H, NCH$_b$(Me)CH$_2$O), 4.03(dd, 1H, NCH(Me)CH$_{ab}$H$_{cd}$O), 3.95(dd, 1H, NCH(Me)CH$_{ab}$H$_{cd}$O), 3.03 (m, 2H, C(N)(CH(CH$_3$)$_2$), 2.39(m, 1H, (CH$_3$)$_2$CH$_a$C(O)), 2.30(m, 1H, (CH$_3$)$_2$CH$_b$C(O)), 1.51, 1.41, 1.37(d, 6H, NCH(CH$_3$)CH$_2$O), 1.24–1.13(d*4, 12H, C(N)(CH(CH$_3$)$_2$) 1.04–0.85(d*5, 12H, (CH$_3$)$_2$CHC(O)); $^{13}$C-NMR (50.289 MHz, CDCl$_3$) 183.45, 182.98, 182.81(s, CH$_3$C(O)), 175.95, 175.70, 175.32(s, C(N)CH$_3$), 94.31, 93.84, 93.59(s, C(O)CHC(N)), 76.80, 76.69, 76.36(s, NCH(Me)CH$_2$O), 64.77, 64.36, 63.59(s, NCH(Me)CH$_2$O), 36.46, 36.36, 36.22(s, (CH$_3$)$_2$CHC(O)), 31.20, 31.00, 30.90(s, C(N)CH(CH$_3$)$_2$), 22.32, 22.17, 22.10, 22.05(s, NCH(CH$_3$)CH$_2$O), 21.87, 21.66, 21.60, 21.50(s, C(N)CH(CH$_3$)$_2$), 20.89, 20.78, 20.63, 20.52(s, (CH$_3$)$_2$CHC(O)); EA (cal C: 61.27, H: 9.00, N: 5.95, found C: 61.33, H: 9.48, N: 5.72).

EXAMPLE 19

Preparation of Ti((CH$_3$)$_3$CC(O)CHC(NCH$_2$CH$_2$O) CH$_3$)$_2$, Ti(22dmeih)$_2$ This Example was carried out according to the same procedure as in Example 11, using 4.98 g (26.88 mmol) of (CH$_3$)$_3$CC(O)CHCCH$_3$(HNCH$_2$CH$_2$OH) prepared in Example 9 and 3.82 g (13.44 mmol) of Ti(O-iPr)$_4$. Thus, 5.05 g (90.66% yield) of Ti((CH$_3$)$_3$CC(O)CHC(NCH$_2$CH$_2$O)CH$_3$)$_2$ was obtained.

NMR results measured for the product are as follows:
$^1$H-NMR (199.976 MHz, CDCl$_3$) 5.18(s, 2H, C(O)CHC(N)), 4.44–4.26(ddt, 4H, NCH$_2$CH$_2$O), 4.03–3.82 (ddt, 4H, NCH$_2$CH$_2$O), 2.00 (s, 6H, C(N)CH$_3$), 0.92(s, 18H, (CH$_3$)$_3$CC(O)); $^{13}$C-NMR (50.289 MHz, CDCl$_3$) 184.48(s, (CH$_3$)$_3$CC(O)), 168.87(s, C(N)CH$_3$), 97.01(s, C(O)CHC(N)), 70.89 (s, NCH$_2$CH$_2$O), 60.18(s, NCH$_2$CH$_2$O), 37.84(s, (CH$_3$)$_3$CC(O)), 28.04(s, (CH$_3$)$_3$CC(O)), 22.87(s, C(N)CH$_3$); EA (cal C: 57.97, H: 8.27, N: 6.76 found C: 57.87, H: 8.63, N: 6.70).

EXAMPLE 20

Preparation of Ti((CH$_3$)$_3$CC(O)CHC(NCH$_2$CH(Me)O)CH$_3$)$_2$, Ti(22dm2meih)$_2$ This Example was carried out according to the same procedure as in Example 11, using 4.0 g (20.06 mmol) of (CH$_3$)$_3$CC(O)CHCCH$_3$(HNCH$_2$CH(Me)OH) prepared in Example 10 and 2.85 g (10.03 mmol) of Ti(O-iPr)$_4$. Thus, 3.91 g (88.06% yield) of Ti((CH$_3$)$_3$CC(O)CHC(NCH$_2$CH(Me)O)CH$_3$)$_2$ was obtained.

NMR results measured for the product are as follows:
$^1$H-NMR (199.976 MHz, CDCl$_3$) 5.30, 5.28, 5.23, 5.19(s, 2H, C(O)CHC(N)), 4.91, 4.82 (m, 2H, NCH$_2$CH(Me)O), 4.16(dd, 1H, NCH$_{ab}$H$_{cd}$CH(Me)O), 3.98(dd, 1H, NCH$_{ab}$H$_{cd}$CH(Me)O), 3.77(dd, 1H, NCH$_{ab}$H$_{cd}$CH(Me)O), 3.63(dd, 1H, NCH$_{ab}$H$_{cd}$CH(Me)O), 2.07, 2.06, 2.04(s, 6H, C(N)CH$_3$), 1.22–1.14(d, 6H, NCH$_2$CH(CH$_3$)O), 1.02, 1.01, 1.00, 1.00(s, 18H, (CH$_3$)$_3$CC(O)); $^{13}$C-NMR (50.289 MHz, CDCl$_3$) 185.12(s, (CH$_3$)$_3$CC(O)), 168.79, 168.46, 168.17(s, C(N)CH$_3$), 97.47, 97.00, 96.89(s, C(O)CHC(N)), 77.31, 76.80, 76.36(s, NCH$_2$CH(Me)O), 67.53, 66.95, 66.57, 66.36 (s, NCH$_2$CH(Me)O), 38.29, 38.22(s, (CH$_3$)$_3$CC(O)), 28.50 (s, (CH$_3$)$_3$CC(O)), 23.13, 23.04(s, C(N)CH$_3$), 22.02, 21.18, 20.73(s, NCH$_2$CH(CH$_3$)O); EA (cal C: 59.73, H: 8.66, N: 6.33 found C: 59.44, H: 8.78, N: 6.84).

Table 1 below shows representative examples and physical properties of the titanium precursors according to the present invention. Table 2 below shows representative examples and physical properties of various metal precursors (including a titanium precursor commercially available from Asahi Denka Kogyo K. K., Japan) according to the prior art.

TABLE 1

Titanium Precursors of the Present Invention

| Formula | Abbreviated name (Example No.) | Melting point (° C.) | Vaporization temp. (° C.) | Residue amount (%) |
|---|---|---|---|---|
| (structure) | Ti(eip)$_2$[1] (Example 11) | 199 | 323 | 8.0 |
| (structure) | Ti(2meip)$_2$[2] (Example 12) | 199 | 290 | <0.5 |
| (structure) | Ti(1meip)$_2$[3] (Example 13) | 61* | 295 | 3.3 |
| (structure) | Ti(1deip)$_2$[4] (Example 14) | 235 | 290 | 13.7 |
| (structure) | Ti(1eeip)$_2$[5] (Example 15) | 149 | 303 | 7.6 |

TABLE 1-continued
Titanium Precursors of the Present Invention
| Formula | Abbreviated name (Example No.) | Melting point (° C.) | Vaporization temp. (° C.) | Residue amount (%) |
|---|---|---|---|---|
| 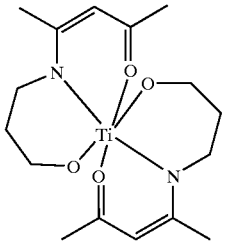 | Ti(pip)$_2$[6] (Example 16) | — | — | 26.6 |
| 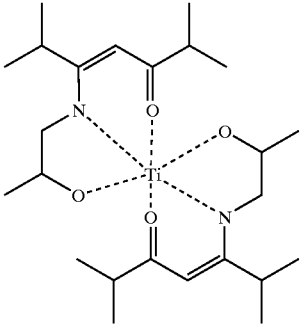 | Ti(26dm2meih)$_2$[7] (Example 17) | 185* | 283 | 8.3 |
| 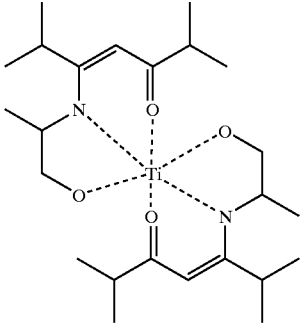 | Ti(26dm1meih)$_2$[8] (Example 18) | 164 | 285 | 3.6 |
| 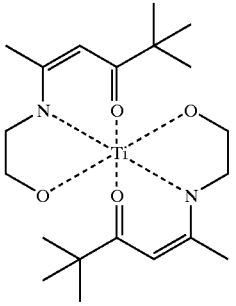 | Ti(22dmeih)$_2$[9] (Example 19) | 180 | 307 | 10.6 |

TABLE 1-continued

Titanium Precursors of the Present Invention

| Formula | Abbreviated name (Example No.) | Melting point (° C.) | Vaporization temp. (° C.) | Residue amount (%) |
|---|---|---|---|---|
| | Ti(22dm2meih)$_2$[10] (Example 20) | 218 | 287 | 0.5 |

[1] Ti(eip)$_2$: Titanium bis[4-(ethoxy)imino-2-pentanoate]
[2] Ti(2meip)$_2$: Titanium bis[4-(2-methylethoxy)imino-2-pentanoate]
[3] Ti(1meip)$_2$: Titanium bis[4-(1-methylethoxy)imino-2-pentanoate]
[4] Ti(1deip)$_2$: Titanium bis[4-(1,1-dimethylethoxy)imino-2-pentanoate]
[5] Ti(1eeip)$_2$: Titanium bis[4-(1-ethylethoxy)imino-2-pentanoate]
[6] Ti(pip)$_2$: Titanium bis[4-(n-propoxy)imino-2-pentanoate]
[7] Ti(26dm2meih)$_2$: Titanium bis[2,6-dimethyl-5-(2-methylethoxy)imino-3-heptanoate]
[8] Ti(26dm1meih)$_2$: Titanium bis[2,6-dimethyl-5-(1-methylethoxy)imino-3-heptanoate]
[9] Ti(22meih)$_2$: Titanium bis[2,2-dimethyl-5-(ethoxy)imino-3-heptanoate]
[10] Ti(22dm2meih)$_2$: Titanium bis[2,2-dimethyl-5-(2-methylethoxy)imino-3-heptanoate]

TABLE 2

Metal Precursors of the Prior Art

| Formula | Abbreviated name | Melting point (° C.) | Vaporization temp. (° C.) | Residue amount (%) |
|---|---|---|---|---|
| | Ba(methd)$_2$[1] | Highly viscous liquid | 391 | 8.3 |
| | Sr(methd)$_2$[2] | Highly viscous liquid | 389 | 3.1 |

TABLE 2-continued

Metal Precursors of the Prior Art

| Formula | Abbreviated name | Melting point (° C.) | Vaporization temp. (° C.) | Residue amount (%) |
|---|---|---|---|---|
| [structure] | Ti(mpd)(thd)$_2$[3] | Highly viscous liquid | 248 | <0.5 |
| [structure] | Ti(OiPr)$_2$(thd)$_2$[4] | 160 | 240 | 7 |

[1] Ba(methd)$_2$: Barium bis[1-methoxyethoxy-2,2,6,6-tetramethyl-3,5-heptanedionate]
[2] Sr(methd)$_2$: Strontium bis[1-methoxyethoxy-2,2,6,6-tetramethyl-3,5-heptanedionate]
[3] Ti(mpd)(thd)$_2$: Titanium [2-methyl-2,4-dioxy-pentane]-bis[(2,2,6,6-tetramethyl-3,5-heptanedionate)]
[4] Ti(O-iPr)$_2$(thd)$_2$: Titanium bis(iso-propoxide)bis[(2,2,6,6-tetramethyl-3,5-heptanedionate)]

Measurement Method of Physical Properties

The physical properties set forth in Tables 1 and 2 were measured by the following method: the melting point and vaporization temperature were measured from endothermic peaks of TG-DSC curves. However, the values indicated by the symbol * in Table 1 were measured by a melting point-measuring device, because the heat absorption by vaporization occurred along with the melting of the precursors during the measurement. The residue amounts were measured by thermal gravimetric analysis (TGA) under atmospheric pressure (N$_2$, 20 ml/min) and recorded as residual weight of the precursors at 550° C.

EXAMPLE 21
Moisture Proof of Precursor 1.0 g of the precursor Ti(eip)$_2$ prepared in Example 11 and 1.0 of the precursor Ti(2meip)$_2$ prepared in Example 12 were placed in vials, respectively, and left to stand in air for three months or more. The analysis by NMR of the precursors was then carried out. The NMR results showed that there were no peaks of non-coordinated ligands and that peaks of the originally prepared precursors remained. It could be thus found that the precursors according to the present invention were not susceptible to moisture and also had excellent handling and storage properties.

EXAMPLE 22
Solubility of Precursor

To evaluate solubility of precursors required in introducing the precursors in liquid phase for the deposition of thin films, the precursor Ti(eip)$_2$ prepared in Example 11 and the precursor Ti(2meip)$_2$ prepared in Example 12 were dissolved in methanol and n-butyl acetate, respectively. Results indicated that 0.5 g of the precursor Ti(eip)$_2$ prepared from the ligand containing no asymmetric carbons was soluble in 5 ml of methanol, but was insoluble in the same amount of n-butyl acetate. In contrast, 0.5 g of the precursor Ti(2meip)$_2$ containing asymmetric carbons on its ligand was soluble in both methanol and n-butyl acetate. Moreover, the precursor Ti(22dm2meih)$_2$ prepared in Example 20 showed enhanced solubility over the precursor Ti(2meip)$_2$ by 20%, due to a t-butyl group in its ligand. It could be accordingly found that the solubility of the precursors was influenced by the kind of R$_1$, R$_2$ and R$_3$ in the above formula (I) and that the presence of asymmetric carbons in particularly R$_1$ and R$_2$ provided an increase in solubility of the precursors.

EXAMPLE 23
Analysis of Thermal Property for Precursor

TG-DSC analysis for the precursor Ti(eip)$_2$ according to Example 11 and the precursor Ti(2meip)$_2$ according to Example 12 was carried out under atmospheric pressure in nitrogen gas or in air, and under a reduced pressure (1.3 mbar) using Netzsch STA 449C equipment. In this analysis, the precursors were heated to 550° C. at a scanning rate of 10° C./min in nitrogen gas of a flow rate of 20 ml/min, or in air of a flow rate of 30 ml/min. The results are shown in FIGS. 1a, 1b, 2a, 2b and 3.

Figure 3:
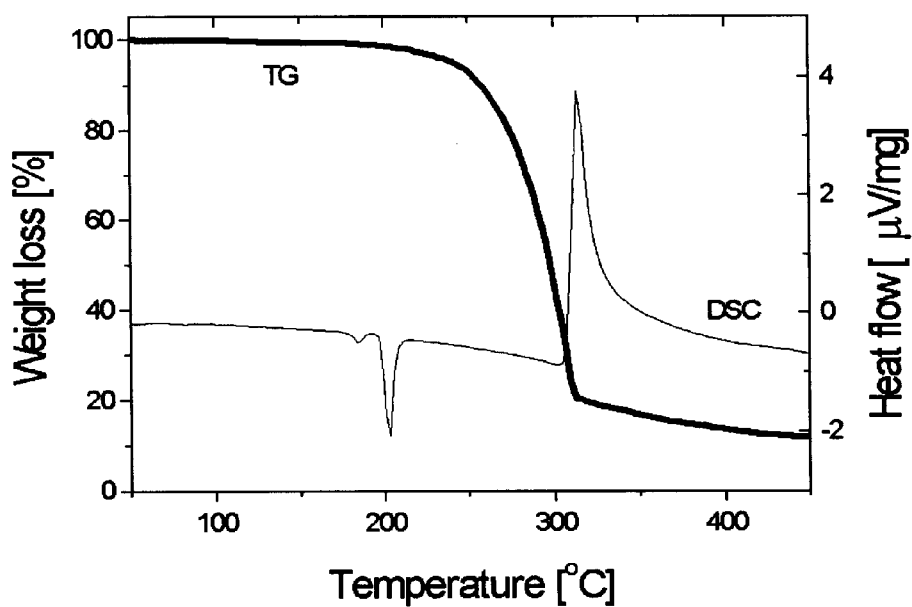
FIG. 3 is a plot of TG-DSC curves according to a temperature rise in air for the precursor Ti(2meip)$_2$ of the present invention.

By the TG-DSC analysis under nitrogen atmosphere, it could be found that the precursor Ti(2meip)$_2$ prepared in Example 12 melted at 190° C. and completely vaporized at about 290° C. (see, FIG. 1b). Additionally, as seen in FIG. 3, by the TG-DSC analysis in air, the precursor Ti(2meip)$_2$ was found to be thermally decomposed with exhibiting a strong exothermic peak at about 315° C. In this regard, the precursor Ti(2meip)$_2$ is clearly distinct from the conventional precursors Ti(thd)$_2$(O-iPr)$_2$ and Ti(thd)$_2$ (mpd) that are thermally decomposed with exhibiting a weak exothermic peak over a wide range of temperature. This difference is due to that Ti(2meip)$_2$ has a relatively weak Ti-N bond compared with a Ti-O bond and has a homoleptic structure.

Figure 4:
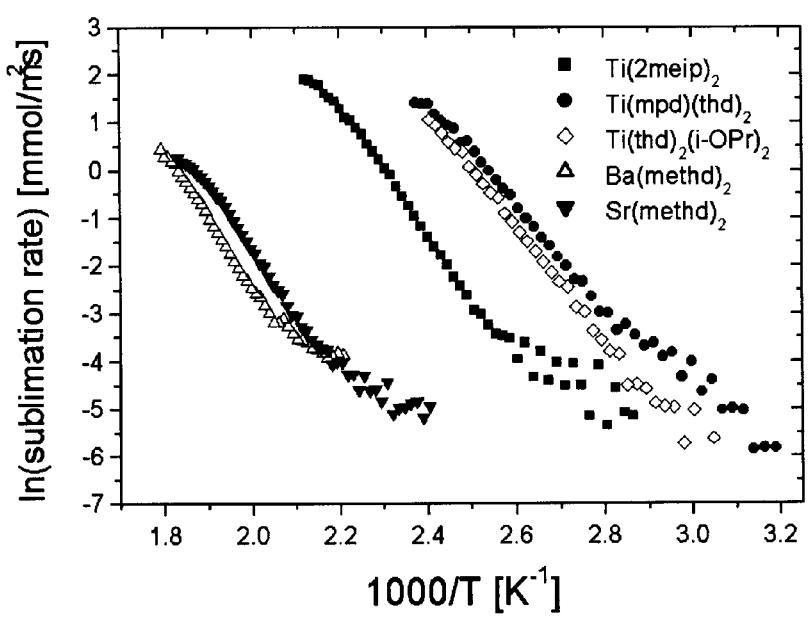
FIG. 4 is a plot of graphs showing vaporization rates according to temperature that are measured in thermogravimetric analysis for the precursor Ti(2meip)$_2$ of the present invention and the commercially available precursors including titanium (2-methyl-2,4-dioxy-pentane)-bis(2,2,6,6-tetramethyl-3,5-heptanedionate)(Ti(mpd)(thd)$_2$), titanium bis(iso-propoxide) bis(2,2,6,6-tetramethyl-3,5-heptanedionate) (Ti(thd)$_2$(O-iPr)$_2$), barium bis(1-methoxyethoxy-2,2,6,6,-tetramethyl-3,5-hetanedionate) (Ba(methd)$_2$), and strontium bis(1-methoxyethoxy-2,2,6,6,-tetramethyl-3,5-hetanedionate)(Sr(methd)$_2$)

Moreover, vaporization rates of the precursor Ti(2meip)$_2$ was compared to that of the commercial precursors Ti(mpd)(thd)$_2$, Ti(thd)$_2$ (O-iPr)$_2$, Ba(methd)$_2$ and Sr(methd)$_2$. The results are shown in FIG. 4. It could be found from FIG. 4 that Ti(2meip)$_2$ was low in their vapor pressure at the respective temperatures as compared to the commercial precursors, so that it would be advantageous to ensure similarity in vaporization property when forming a multi-component thin film with a low volatility metal, such as barium, or strontium, etc.

EXAMPLE 24
Deposition of BST Thin Film by MOCVD Method

Using the precursor Ti(2meip)$_2$ prepared in Example 12 or the commercial precursor Ti(mpd)(thd)$_2$, as a titanium precursor, and Ba(methd)$_2$ and Sr(methd)$_2$, as barium and strontium precursors, thin films of $(Ba_x, Sr_{1-x})Ti_yO_{3-z}$ (BST) were deposited on substrates by a Liquid Source Metal Organic Chemical Vapor Deposition (LS-MOCVD) method. The substrates used in the deposition were planar substrates of Pt(1000 Å)/SiO$_2$(1000 Å)/Si and fine-patterned substrates where Ru is deposited on the patterns having an aspect ratio of 3 (depth/width=0.45 μm/0.15 μm). The Pt film of the substrates was deposited by a sputtering method, and the Ru film by a MOCVD method.

As the liquid precursors, there were used two set of single solutions that had been prepared by dissolving the Ba, Sr and Ti precursors in n-butyl acetate. For the preparation of the single solution, the precursors were used at Set I molar concentrations, i.e., 0.0093 M Ba, 0.0093 M Sr and 0.07999 M Ti(Ba: Sr: Ti=1:1:8.6), or Set II molar concentrations, i.e., 0.0093 M Ba, 0.0093 M Sr and 0.04 M Ti(Ba: Sr: Ti=1:1:4.3).

An input flow rate of the liquid precursors was maintained at a constant value of 0.05 g/min during the deposition of the BST thin film by means of a Liquid MFC (error of ±0.002 g/min) from Lintec Inc.(Japan). To observe a trend of introduction of titanium into the BST films according to a substrate temperature, the depositions were carried out using the Set II solution in a temperature range of 400 to 500° C. For the depositions, MOCVD equipment was used in which a vaporizer, a deposition chamber and a gas delivery tube are all mounted in an oven. Additional process conditions are set forth in Table 3.

TABLE 3

| Process conditions | |
|---|---|
| Deposition pressure | 1 Torr |
| Flow rate of delivery gas N$_2$ | 100 sccm |
| Flow rate of oxidizing agent O$_2$ | 100 sccm |
| Flow rate of N$_2$ introduced to deposition chamber | 100 sccm |
| Input flow rate of precursor solution | 0.05 g/min |
| Temperature of substrate | 400~500° C. |

TABLE 3-continued

| Process conditions | |
|---|---|
| Temperature of vaporization | 280° C. |
| Temperature of precursor solution delivery tube | 280° C. |
| Temperature of volatile gas delivery tube | 150° C. |
| Deposition time | 15 min |

Figure 5A:
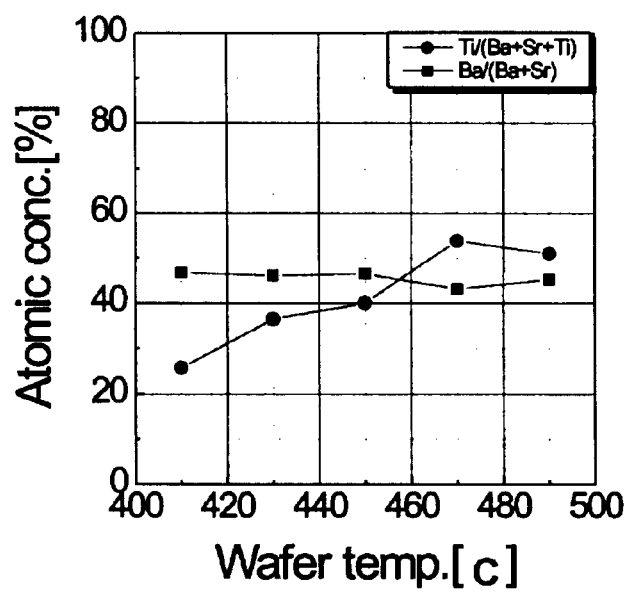
FIG. 5a is a plot of graphs showing a variation in titanium and barium contents according to deposition temperature in depositing a barium strontium titanate (BST) thin film using the precursor Ti(2meip)$_2$ of the present invention.
Figure 5B:
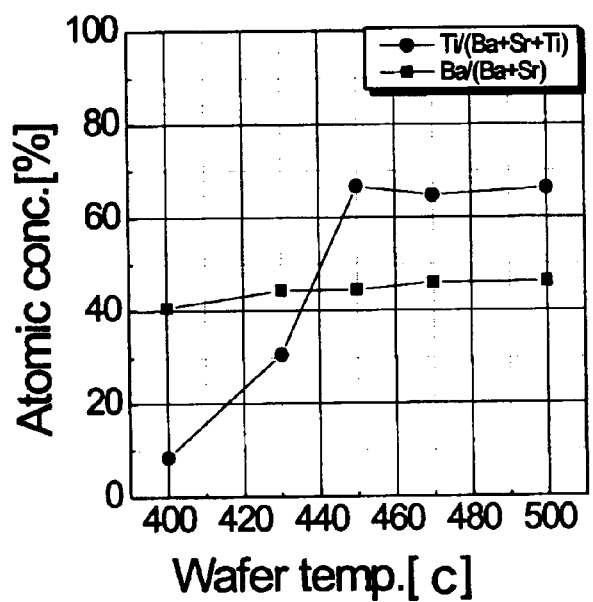
FIG. 5b is a plot of graphs showing a variation in titanium and barium contents according to deposition temperature in depositing a barium strontium titanate (BST) thin film using the prior precursor Ti(mpd)(thd)$_2$.

To analyze the contents of barium, strontium, and titanium in the thin film, the BST thin film deposited on the Pt film of the substrate was etched with a hydrofluoric acid (HF) solution, and then quantitatively analyzed by Inductively Coupled Plasma-Atomic Emission Spectroscopy (ICP-AES). The analytical results are shown in FIGS. 5a and 5b. As seen in FIGS. 5a and 5b, if the commercial titanium precursor was used, the titanium content was significantly dependent on temperature, whereas if the titanium precursor according to the present invention was used, the titanium content was dependent on temperature to a reduced extent. Accordingly, it was found that the use of the prior titanium precursor made it difficult to control the titanium content evenly between devices based on particularly large area substrates, or the titanium content at the upper and lower portions of a high topology device. However, it was found that the use of the titanium precursor according to the present invention solved this problem relating to the titanium content, because the temperature dependence of the titanium content in the thin film was low.

Figure 6:
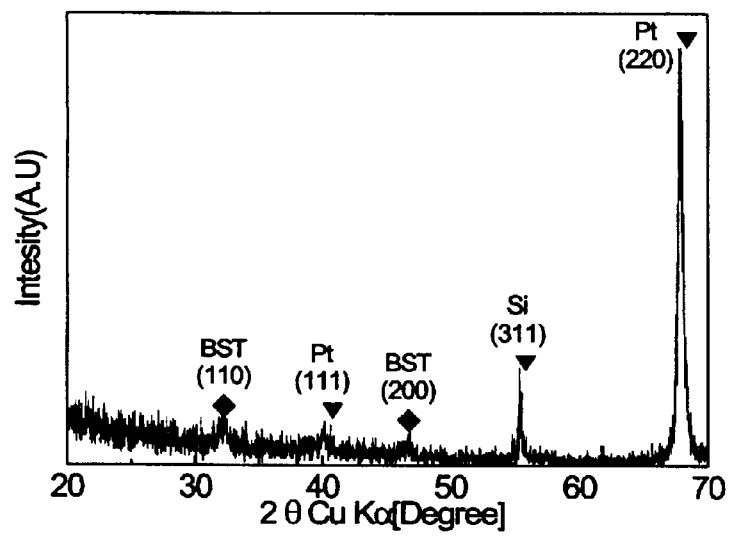
FIG. 6 is a X-Ray Diffraction (XRD) pattern for a BST thin film deposited at 430° C. according to Example 24.
Figure 7A:
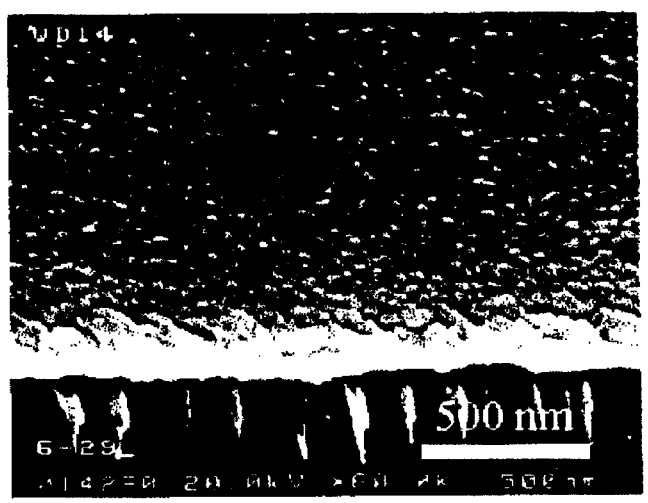
FIG. 7a is a image taken by a scanning electron microscope for a plane of a BST thin film deposited on a planar substrate at 430° C. according to Example 24.
Figure 7B:
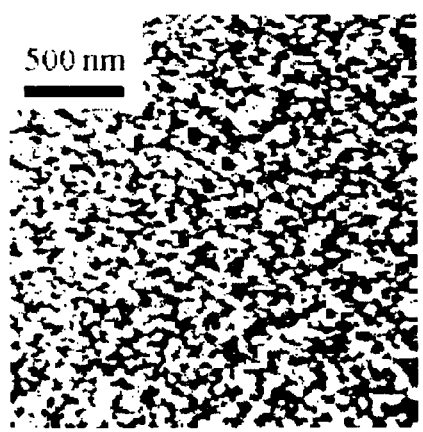
FIG. 7b is a surface image taken by an atomic force microscope (AFM) for a plane of a BST thin film deposited on a planar substrate at 430° C. according to Example 24.
Figure 8:
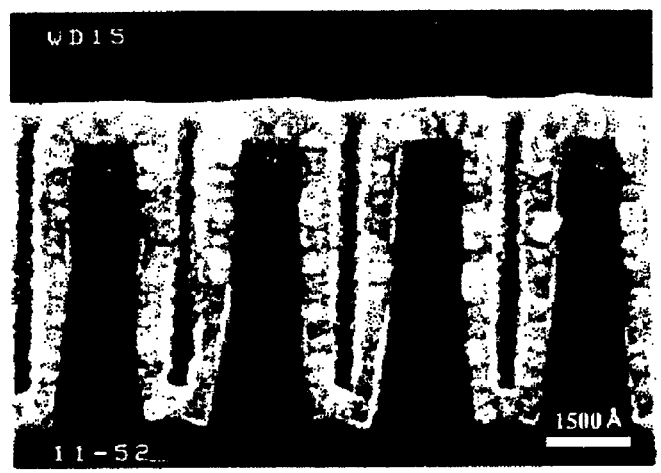
FIG. 8 is a cross sectional image taken by a scanning electron microscope for a BST thin film deposited on a fine-patterned substrate at 430° C. according to Example 24.
Figure 9:
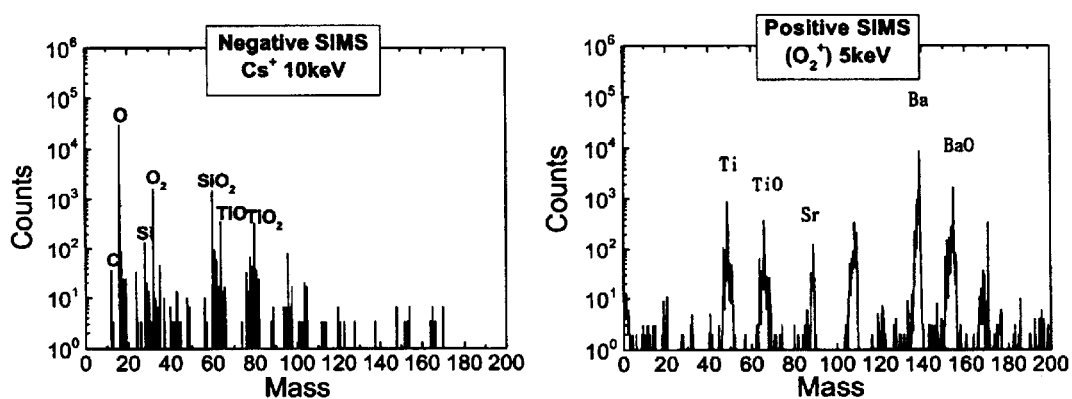
FIG. 9 is a plot that shows analytical results by the Secondary Ion Mass Spectroscopy of a BST thin film deposited at 430° C. according to Example 24.

Among the thin films deposited by the above method, the thin film deposited at 430° C. was subjected to various analyses. FIG. 6 is a graph showing X-ray diffraction (XRD) analysis results for the thin film. It can be found from FIG. 6 that a perovskite crystalline phase was present in the BST thin film which had not been subjected to additional heat-treatment following the deposition. FIG. 7a is a image taken by a scanning electron microscope for a slightly inclined plane of the thin film which was formed on the substrate at 430° C. As seen in FIG. 7a, the thin film had a smooth surface with no protrusions or hazy appearance. FIG. 7b is a image taken by an atomic force microscope (AFM) for the same thin film. FIG. 7b also supports the fact that the surface of the thin film is very smooth so that root mean square (RMS) roughness is no more than 170Å. FIG. 8 is a cross sectional image showing the side of the BST thin film which was formed on the fine-patterned substrate having an aspect ratio of 3. From FIG. 8, it can be seen that the thin film had excellent step coverage. FIG. 9 shows analytical results by Secondary Ion Mass Spectrometry of the thin film. From FIG. 9, it can be seen that the thin film was very low in contamination with carbon or nitrogen atoms of the ligand.

Figure 10:
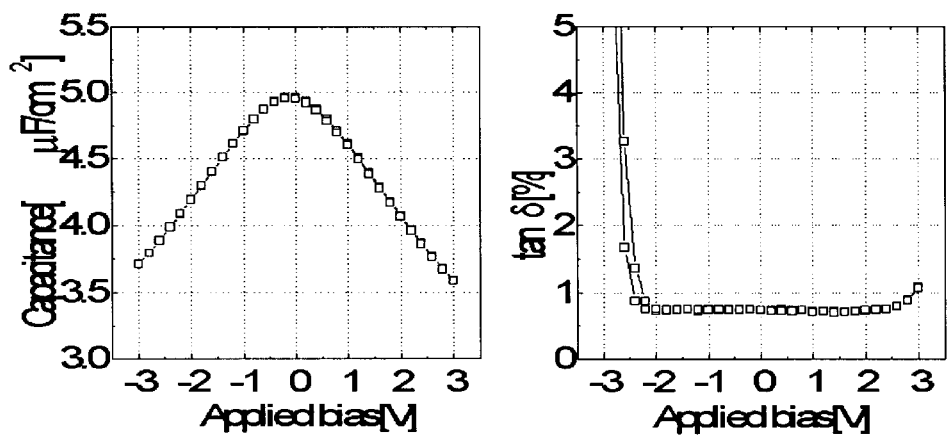
FIG. 10 is a plot that shows the dielectric characteristics of a Pt/BST/Pt capacitor, which has a BST thin film deposited at 430° C. according to Example 24.
Figure 11:
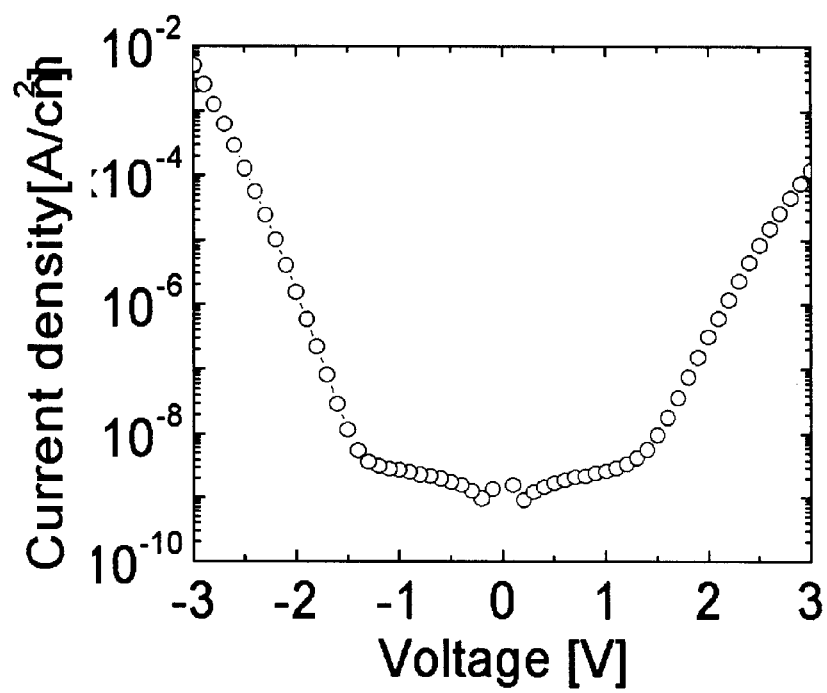
FIG. 11 is a plot that shows leakage current density of a Pt/BST/Pt capacitor, which has a BST thin film deposited at 430° C. according to Example 24.

Moreover, a planar MIM capacitor of a Pt/BST/Pt structure was fabricated using the BST thin film which was deposited at 430° C. from the precursor Ti(2meip)$_2$ according to the present invention. Electrical properties and dielectric properties for the fabricated capacitor were measured. Results are shown in FIGS. 10 and 11. As predicted from a XRD pattern of FIG. 6, the capacitor displayed the typical dielectric properties of perovskite dielectrics in that capacitance was the highest at zero bias and decreased with an increase in the bias. Also, the capacitor exhibited an excellent insulating property in that dielectric loss factor was less than 1% at an operation voltage of highly integrated DRAM devices, ±1V.

As is apparent from the foregoing, the group IV metal precursors according to the present invention has volatility suitable for the formation of a thin film, as well as excellent thermal properties in that it leaves little or no residues after being vaporized and in that it is completely decomposed under an oxygen atmosphere. Furthermore, as the group IV metal precursor according to the present invention has a high chemical stability, it causes no side reaction when being delivered in the gas phase or used along with other precursors. Also, this precursor is not susceptible to moisture and hence requires no efforts for storage and handling. The precursor according to the present invention leaves little or no residues of carbon or nitrogen, particularly when being used for the deposition of a multi-component thin film, such as BST and the like. Further, using the titanium precursor according to the present invention, it is easy to control the titanium content throughout a large area thin film or at the upper and lower portions of a high topology thin film. Thus, this precursor enables the formation of a high quality metal oxide thin film which is excellent in step coverage and surface structure.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A chemical vapor deposition method which comprises forming a metal oxide thin film using, as a group IV metal precursor, a complex of a formula $M(L)_2$ in which M is a group IV metal ion having a charge of +4 and L is a tridentate ligand having a charge of −2, the ligand being represented by the following formula (I):

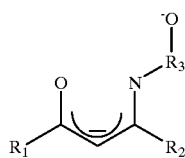

(I)

wherein each of $R_1$ and $R_2$, independently, is a linear or branched $C_{1-8}$ alkyl group; and $R_3$ is a linear or branched $C_{1-8}$ alkylene group.

2. The chemical vapor deposition method according to claim 1, wherein M is Ti.

3. The chemical vapor deposition method according to claim 1, which comprises vaporizing the precursor by using of a bubbler or a vaporizer.

4. The chemical vapor deposition method according to claim 1, in which the metal oxide thin film is a multi-component thin film containing a group IV metal.

5. The chemical vapor deposition method according to claim 1, in which the metal oxide thin film is a multi-component thin film containing titanium.

6. A metal oxide thin film formed by utilizing an organometallic precursor of the formula $M(L)_2$ in which M is a group IV metal ion having a charge of +4 and L is a tridentate ligand having a charge of −2, the ligand being represented by the following formula (I):

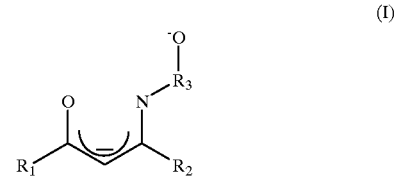

(I)

wherein each of $R_1$ and $R_2$, independently, is a linear or branched $C_{1-8}$ alkyl group; and $R_3$ is a linear or branched $C_{1-8}$ alkylene group.

7. The organometallic precursor of claim 1, wherein said titanium precursor is selected from the group consisting of titanium bis [4-(ethoxy)imino-2-pentanoate], titanium bis [4-(2-methylethoxy)imino-2-pentanoate], titanium bis [4-(1-methylethoxy)imino-2-pentanoate], titanium bis [4-(1,1-dimethylethoxy)imino-2-pentanoate], titanium bis [4-(1-ethylethoxy)imino-2-pentanoate], titanium bis [4-(n-propoxy) imino-2-pentanoate], titanium bis [2,6-dimethyl-5-(2-methylethoxy)imino-3-heptanoate], titanium bis[2,6-dimethyl-5-(1-methylethoxy)imino-3-heptanoate], titanium bis[2,2-dimethyl-5-(ethoxy)imino-3-heptanoate]and titanium bis[2,2-dimethyl-5-(2-methylethoxy)imino-3-heptanoate].

* * * * *